(12) United States Patent
Allen, IV

(10) Patent No.: US 10,856,933 B2
(45) Date of Patent: Dec. 8, 2020

(54) SURGICAL INSTRUMENT HOUSING INCORPORATING A CHANNEL AND METHODS OF MANUFACTURING THE SAME

(71) Applicant: COVIDIEN LP, Mansfield, MA (US)

(72) Inventor: James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 472 days.

(21) Appl. No.: 15/627,714

(22) Filed: Jun. 20, 2017

(65) Prior Publication Data

US 2018/0036024 A1 Feb. 8, 2018

Related U.S. Application Data

(60) Provisional application No. 62/370,057, filed on Aug. 2, 2016.

(51) Int. Cl.
*A61B 18/14* (2006.01)
*A61B 18/00* (2006.01)
(Continued)

(52) U.S. Cl.
CPC .......... *A61B 18/1445* (2013.01); *A61B 34/30* (2016.02); *A61B 2017/2948* (2013.01);
(Continued)

(58) Field of Classification Search
CPC ................ A61B 18/1445; A61B 34/30; A61B 2018/00029; A61B 2018/00178;
(Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CA | 2104423 A1 | 2/1994 |
| DE | 2415263 A1 | 10/1975 |

(Continued)

*Primary Examiner* — Jaymi E Della
*Assistant Examiner* — Sean W Collins
(74) *Attorney, Agent, or Firm* — Carter, DeLuca & Farrell LLP

(57) ABSTRACT

A surgical device includes a housing, at least one electrical wire, a shaft, and an end effector assembly. The housing defines an interior cavity and first and second housing portions. The first and second housing portions are configured to engage one another to enclose the interior cavity. A channel is defined within an outer perimeter of the first and/or second housing portion such that engagement of the first and second housing portions encloses the channel separate from the interior cavity. The electrical wire(s) is housed within the channel and adapted to connect to a source of energy. The shaft is coupled to the housing and extends distally therefrom. The end effector assembly is disposed at a distal end of the shaft, wherein the end effector assembly is electrically coupled to the at least one electrical wire for supplying energy to the end effector assembly.

20 Claims, 6 Drawing Sheets

(51) Int. Cl.
*A61B 34/30* (2016.01)
*A61B 17/29* (2006.01)

(52) U.S. Cl.
CPC .............. *A61B 2018/00029* (2013.01); *A61B 2018/0091* (2013.01); *A61B 2018/00178* (2013.01); *A61B 2218/002* (2013.01); *A61B 2218/007* (2013.01)

(58) Field of Classification Search
CPC ...... A61B 2018/0091; A61B 2218/002; A61B 2218/007; A61B 2017/2948
See application file for complete search history.

(56) References Cited

U.S. PATENT DOCUMENTS

| | | | |
|---|---|---|---|
| 728,883 | A | 5/1903 | Downes |
| 1,586,645 | A | 6/1926 | Bierman |
| 1,813,902 | A | 7/1931 | Bovie |
| 2,002,594 | A | 5/1935 | Wappler et al. |
| 2,011,169 | A | 8/1935 | Wappler |
| 2,031,682 | A | 2/1936 | Wappler et al. |
| 2,176,479 | A | 10/1939 | Mills |
| 2,279,753 | A | 4/1942 | Knopp |
| 2,305,156 | A | 12/1942 | Grubel |
| 2,632,661 | A | 3/1953 | Cristofv |
| 2,668,538 | A | 2/1954 | Baker |
| 2,796,065 | A | 6/1957 | Kapp |
| 3,459,187 | A | 8/1969 | Pallotta |
| 3,643,663 | A | 2/1972 | Sutter |
| 3,651,811 | A | 3/1972 | Hildebrandt et al. |
| 3,720,896 | A | 3/1973 | Beierlein |
| 3,862,630 | A | 1/1975 | Balamuth |
| 3,863,339 | A | 2/1975 | Reaney et al. |
| 3,866,610 | A | 2/1975 | Kletschka |
| 3,911,766 | A | 10/1975 | Fridolph et al. |
| 3,920,021 | A | 11/1975 | Hiltebrandt |
| 3,921,641 | A | 11/1975 | Hulka |
| 3,938,527 | A | 2/1976 | Rioux et al. |
| 3,952,749 | A | 4/1976 | Fridolph et al. |
| 3,970,088 | A | 7/1976 | Morrison |
| 3,987,795 | A | 10/1976 | Morrison |
| 4,005,714 | A | 2/1977 | Hiltebrandt |
| 4,041,952 | A | 8/1977 | Morrison, Jr. et al. |
| 4,043,342 | A | 8/1977 | Morrison, Jr. |
| 4,074,718 | A | 2/1978 | Morrison, Jr. |
| 4,088,134 | A | 5/1978 | Mazzariello |
| 4,112,950 | A | 9/1978 | Pike |
| 4,127,222 | A | 11/1978 | Adams |
| 4,128,099 | A | 12/1978 | Bauer |
| 4,165,746 | A | 8/1979 | Burgin |
| 4,233,734 | A | 11/1980 | Bies |
| 4,300,564 | A | 11/1981 | Furihata |
| D263,020 | S | 2/1982 | Rau, III |
| 4,370,980 | A | 2/1983 | Lottick |
| 4,375,218 | A | 3/1983 | DiGeronimo |
| 4,416,276 | A | 11/1983 | Newton et al. |
| 4,418,692 | A | 12/1983 | Guay |
| 4,452,246 | A | 6/1984 | Bader et al. |
| 4,492,231 | A | 1/1985 | Auth |
| 4,552,143 | A | 11/1985 | Lottick |
| 4,574,804 | A | 3/1986 | Kurwa |
| 4,597,379 | A | 7/1986 | Kihn et al. |
| 4,600,007 | A | 7/1986 | Lahodny et al. |
| 4,655,215 | A | 4/1987 | Pike |
| 4,655,216 | A | 4/1987 | Tischer |
| 4,657,016 | A | 4/1987 | Garito et al. |
| 4,662,372 | A | 5/1987 | Sharkany et al. |
| 4,671,274 | A | 6/1987 | Sorochenko |
| 4,685,459 | A | 8/1987 | Koch et al. |
| D295,893 | S | 5/1988 | Sharkany et al. |
| D295,894 | S | 5/1988 | Sharkany et al. |
| 4,754,892 | A | 7/1988 | Retief |
| 4,763,669 | A | 8/1988 | Jaeger |
| 4,827,929 | A | 5/1989 | Hodge |
| 4,846,171 | A | 7/1989 | Kauphusman et al. |
| 4,887,612 | A | 12/1989 | Esser et al. |
| 4,938,761 | A | 7/1990 | Ensslin |
| 4,985,030 | A | 1/1991 | Melzer et al. |
| 5,007,908 | A | 4/1991 | Rydell |
| 5,026,370 | A | 6/1991 | Lottick |
| 5,035,695 | A | 7/1991 | Weber, Jr. et al. |
| 5,084,057 | A | 1/1992 | Green et al. |
| 5,099,840 | A | 3/1992 | Goble et al. |
| 5,116,332 | A | 5/1992 | Lottick |
| 5,147,357 | A | 9/1992 | Rose et al. |
| 5,151,102 | A | 9/1992 | Kamiyama et al. |
| 5,176,695 | A | 1/1993 | Dulebohn |
| 5,190,541 | A | 3/1993 | Abele et al. |
| 5,196,009 | A | 3/1993 | Kirwan, Jr. |
| 5,197,964 | A | 3/1993 | Parins |
| 5,215,101 | A | 6/1993 | Jacobs et al. |
| 5,217,457 | A | 6/1993 | Delahuerga et al. |
| 5,217,458 | A | 6/1993 | Parins |
| 5,217,460 | A | 6/1993 | Knoepfler |
| 5,219,354 | A | 6/1993 | Choudhury et al. |
| 5,244,462 | A | 9/1993 | Delahuerga et al. |
| 5,250,047 | A | 10/1993 | Rydell |
| 5,250,063 | A | 10/1993 | Abidin et al. |
| 5,258,001 | A | 11/1993 | Corman |
| 5,258,006 | A | 11/1993 | Rydell et al. |
| 5,261,918 | A | 11/1993 | Phillips et al. |
| 5,275,615 | A | 1/1994 | Rose |
| 5,277,201 | A | 1/1994 | Stern |
| 5,282,799 | A | 2/1994 | Rydell |
| 5,290,286 | A | 3/1994 | Parins |
| 5,304,203 | A | 4/1994 | El-Mallawany et al. |
| 5,308,357 | A | 5/1994 | Lichtman |
| 5,312,433 | A | 5/1994 | Boebel et al. |
| 5,314,445 | A | 5/1994 | Heidmueller nee Degwitz et al. |
| 5,318,589 | A | 6/1994 | Lichtman |
| 5,324,289 | A | 6/1994 | Eggers |
| 5,326,806 | A | 7/1994 | Yokoshima et al. |
| 5,330,471 | A | 7/1994 | Eggers |
| 5,334,183 | A | 8/1994 | Wuchinich |
| 5,334,215 | A | 8/1994 | Chen |
| 5,336,220 | A | 8/1994 | Ryan et al. |
| 5,336,221 | A | 8/1994 | Anderson |
| 5,342,359 | A | 8/1994 | Rydell |
| 5,342,381 | A | 8/1994 | Tidemand |
| 5,342,393 | A | 8/1994 | Stack |
| 5,344,424 | A | 9/1994 | Roberts et al. |
| 5,352,222 | A | 10/1994 | Rydell |
| 5,354,271 | A | 10/1994 | Voda |
| 5,356,408 | A | 10/1994 | Rydell |
| 5,366,477 | A | 11/1994 | LeMarie, III et al. |
| 5,368,600 | A | 11/1994 | Failla et al. |
| 5,376,089 | A | 12/1994 | Smith |
| 5,383,897 | A | 1/1995 | Wholey |
| 5,389,098 | A | 2/1995 | Tsuruta et al. |
| 5,389,104 | A | 2/1995 | Hahnen et al. |
| 5,391,166 | A | 2/1995 | Eggers |
| 5,391,183 | A | 2/1995 | Janzen et al. |
| 5,396,900 | A | 3/1995 | Slater et al. |
| 5,403,312 | A | 4/1995 | Yates et al. |
| 5,411,519 | A | 5/1995 | Tovey et al. |
| 5,411,520 | A | 5/1995 | Nash et al. |
| 5,413,571 | A | 5/1995 | Katsaros et al. |
| 5,415,657 | A | 5/1995 | Taymor-Luria |
| 5,422,567 | A | 6/1995 | Matsunaga |
| 5,423,810 | A | 6/1995 | Goble et al. |
| 5,425,690 | A | 6/1995 | Chang |
| 5,425,739 | A | 6/1995 | Jessen |
| 5,429,616 | A | 7/1995 | Schaffer |
| 5,431,672 | A | 7/1995 | Cote et al. |
| 5,431,674 | A | 7/1995 | Basile et al. |
| 5,437,292 | A | 8/1995 | Kipshidze et al. |
| 5,438,302 | A | 8/1995 | Goble |
| 5,441,517 | A | 8/1995 | Kensey et al. |
| 5,443,463 | A | 8/1995 | Stern et al. |
| 5,443,464 | A | 8/1995 | Russell et al. |
| 5,443,480 | A | 8/1995 | Jacobs et al. |
| 5,445,638 | A | 8/1995 | Rydell et al. |
| 5,445,658 | A | 8/1995 | Durrfeld et al. |

(56) References Cited

U.S. PATENT DOCUMENTS

| | | |
|---|---|---|
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Shame et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,620,453 A | 4/1997 | Nallakrishnan |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| H001745 H | 8/1998 | Paraschac |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,876,401 A | 3/1999 | Schulze et al. |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,939 A | 11/1999 | Yoon |
| 5,989,277 A | 11/1999 | LeMaire, III et al. |
| 3,004,335 A | 12/1999 | Vaitekunas et al. |
| 5,997,565 A | 12/1999 | Inoue |
| 3,010,516 A | 1/2000 | Hulka |
| 6,024,741 A | 2/2000 | Williamson, IV et al. |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |

(56) References Cited

U.S. PATENT DOCUMENTS

| | | |
|---|---|---|
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H001904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H002037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Komerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Trudcai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |

(56) References Cited

U.S. PATENT DOCUMENTS

| | | | |
|---|---|---|---|
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 8,192,433 B2 | 6/2012 | Johnson et al. |
| 8,540,711 B2 | 9/2013 | Dycus et al. |
| 8,905,977 B2 * | 12/2014 | Shelton | A61B 17/07207 604/131 |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Trudcai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0162557 A1 | 8/2004 | Tetzlaff et al. |
| 2004/0193153 A1 | 9/2004 | Sartor et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter et al. |
| 2005/0004564 A1 | 1/2005 | Wham et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0032785 A1 * | 2/2007 | Diederich | A61B 18/04 606/27 |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |

(56) References Cited

U.S. PATENT DOCUMENTS

| | | | |
|---|---|---|---|
| 2008/0021450 A1 | 1/2008 | Couture | |
| 2008/0033428 A1 | 2/2008 | Artale et al. | |
| 2008/0039835 A1 | 2/2008 | Johnson et al. | |
| 2008/0058802 A1 | 3/2008 | Couture et al. | |
| 2008/0082100 A1 | 4/2008 | Orton et al. | |
| 2010/0179540 A1* | 7/2010 | Marczyk | A61B 18/1445 606/41 |
| 2011/0054472 A1* | 3/2011 | Romero | A61B 18/1442 606/51 |
| 2011/0306967 A1* | 12/2011 | Payne | A61B 18/1445 606/41 |
| 2013/0345701 A1* | 12/2013 | Allen, IV | A61B 18/082 606/41 |
| 2015/0141980 A1* | 5/2015 | Jadhav | A61B 18/1445 606/37 |
| 2015/0297228 A1* | 10/2015 | Huitema | A61B 17/0682 227/176.1 |
| 2016/0174819 A1* | 6/2016 | Ouyang | A61B 1/00103 600/105 |
| 2017/0196635 A1* | 7/2017 | Brennan | A61B 18/1445 |

FOREIGN PATENT DOCUMENTS

| | | |
|---|---|---|
| DE | 2627679 A1 | 1/1977 |
| DE | 8712328 U1 | 2/1988 |
| DE | 04303882 C2 | 2/1995 |
| DE | 29616210 U1 | 11/1996 |
| DE | 19608716 C1 | 4/1997 |
| DE | 19751106 A1 | 5/1998 |
| DE | 19751108 A1 | 5/1999 |
| EP | 0572131 A1 | 12/1993 |
| EP | 0584787 A1 | 3/1994 |
| EP | 0589453 A3 | 4/1994 |
| EP | 0624348 A3 | 6/1995 |
| EP | 0364216 B1 | 1/1996 |
| EP | 0518230 B1 | 5/1996 |
| EP | 0541930 B1 | 3/1998 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 | 7/2003 |
| EP | 1486177 | 6/2004 |
| EP | 1472984 | 11/2004 |
| EP | 0754437 B2 | 12/2004 |
| EP | 1025807 B1 | 12/2004 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1609430 | 12/2005 |
| EP | 1034746 B1 | 3/2006 |
| EP | 1632192 | 3/2006 |
| EP | 1645238 | 4/2006 |
| EP | 1645240 | 4/2006 |
| EP | 0875209 B1 | 5/2006 |
| EP | 1707143 | 10/2006 |
| GB | 2213416 A | 8/1989 |
| GB | 2214430 A | 9/1989 |
| JP | 61-501068 | 9/1984 |
| JP | 6-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | H08-56955 | 5/1996 |
| JP | 08252263 A | 10/1996 |
| JP | 910223 | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 89/00757 | 1/1989 |
| WO | 92/04873 | 4/1992 |
| WO | 92/06642 | 4/1992 |
| WO | 94/08524 | 4/1994 |
| WO | 94/20025 | 9/1994 |
| WO | 95/02369 | 1/1995 |
| WO | 95/07662 | 3/1995 |
| WO | 95/15124 | 6/1995 |
| WO | 96/05776 | 2/1996 |
| WO | 96/022056 | 7/1996 |
| WO | 96/13218 | 9/1996 |
| WO | 97/00646 | 1/1997 |
| WO | 97/00647 | 1/1997 |
| WO | 97/10764 | 3/1997 |
| WO | 97/24073 | 7/1997 |
| WO | 97/24993 | 7/1997 |
| WO | 98/27880 | 7/1998 |
| WO | 99/03407 | 1/1999 |
| WO | 99/03408 | 1/1999 |
| WO | 99/03409 | 1/1999 |
| WO | 99/12488 | 3/1999 |
| WO | 99/40857 | 8/1999 |
| WO | 99/40861 | 8/1999 |
| WO | 99/51158 | 10/1999 |
| WO | 99/66850 | 12/1999 |
| WO | 00/24330 | 5/2000 |
| WO | 00/24331 | 5/2000 |
| WO | 00/41638 | 7/2000 |
| WO | 00/47124 | 8/2000 |
| WO | 00/53112 | 9/2000 |
| WO | 01/17448 | 3/2001 |
| WO | 0154604 A1 | 8/2001 |
| WO | 02/07627 | 1/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080794 | 10/2002 |
| WO | 02/80795 | 10/2002 |
| WO | 02/080796 | 10/2002 |
| WO | 02/080797 | 10/2002 |
| WO | 02/080798 | 10/2002 |
| WO | 02/080799 | 10/2002 |
| WO | 02/081170 | 10/2002 |
| WO | 02080793 A1 | 10/2002 |
| WO | 03/101311 | 12/2003 |
| WO | 03/090630 A3 | 4/2004 |
| WO | 2004/032776 A1 | 4/2004 |
| WO | 2004/032777 A1 | 4/2004 |
| WO | 2004/052221 A1 | 6/2004 |
| WO | 2004/073488 A2 | 9/2004 |
| WO | 2004/073490 A2 | 9/2004 |
| WO | 2004/073753 A2 | 9/2004 |
| WO | 2004/082495 A1 | 9/2004 |
| WO | 2004/098383 A2 | 11/2004 |
| WO | 2004/103156 A2 | 12/2004 |
| WO | 2005/004734 A1 | 1/2005 |

(56) References Cited

FOREIGN PATENT DOCUMENTS

| WO | 2005/004735 A1 | 1/2005 |
| WO | 05110264 A3 | 4/2006 |

* cited by examiner

SURGICAL INSTRUMENT HOUSING INCORPORATING A CHANNEL AND METHODS OF MANUFACTURING THE SAME

CROSS REFERENCE TO RELATED APPLICATION

The present application claims the benefit of and priority to U.S. Provisional Application Ser. No. 62/370,057, filed on Aug. 2, 2016, the entire contents of which are incorporated herein by reference.

BACKGROUND

Technical Field

The present disclosure relates to surgical instruments and, more particularly, to surgical forceps configured for treating and/or cutting tissue incorporating a channel in the housing(s) thereof, and methods of manufacturing the same.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue. Typically, once tissue is treated, the surgeon has to accurately sever the tissue. Accordingly, many devices have been designed which incorporate a knife or blade member which effectively severs tissue after treatment thereof.

As an alternative to open forceps for use with open surgical procedures, many modern surgeons use endoscopic or laparoscopic instruments for remotely accessing tissue through smaller, puncture-like incisions or natural orifices. As a direct result thereof, patients tend to benefit from less scarring and reduced healing time. Endoscopic instruments are typically inserted into the patient through a cannula, or port. Smaller cannulas are usually preferred, which, as can be appreciated, ultimately present a design challenge to instrument manufacturers who must find ways to make endoscopic instruments that fit through the smaller cannulas without compromising functionality.

Currently, energy-based surgical forceps are designed to include one or more hollow or semi-hollow housings, which typically house a handle assembly, an actuation assembly, a rotating assembly, an activation switch, and/or an electric cable which supplies electric power to the energy-based surgical forceps.

SUMMARY

In accordance with the present disclosure, a surgical device is provided including a housing defining an interior cavity. The housing includes a first housing portion and a second housing portion. The first and second housing portions are configured to engage one another to enclose the interior cavity of the housing. A channel is defined within an outer perimeter of at least one of the first housing portion or the second housing portion, wherein engagement of the first and second housing portions encloses the channel such that the channel is separate from the interior cavity of the housing. There is at least one electrical wire housed within the channel, wherein the at least one electrical wire is adapted to connect to a source of energy. A shaft is coupled to the housing and extends distally therefrom. An end effector assembly is disposed at a distal end of the shaft, wherein the end effector assembly is electrically coupled to the at least one electrical wire for supply energy to the end effector assembly.

In an aspect of the present disclosure, the first housing portion and the second housing portion each include a distal end defining a C-shaped aperture, wherein the C-shaped apertures cooperate to define an aperture for receipt of the shaft therethrough upon engagement of the first and second housing portions.

In another aspect of the present disclosure, the first housing portion defines a first channel portion, the second housing portion defines a second channel portion, and wherein the first and second channel portions cooperate to define the channel upon engagement of the first and second housing portions. The first and second channel portions each form one-half of the channel. In one embodiment, the first housing portion and the second housing portion may be configured to engage one another via snap-fitting. In another embodiment, the first housing portion and the second housing portion may be configured to engage one another via an adhesive, wherein the adhesive is selected from a group consisting of epoxy, acrylic, urethane, and cyanoacrylate.

In yet another aspect of the present disclosure, a surgical device is provided including a housing defining an interior cavity. The housing including a first housing portion and a second portion. The first and second housing portions configured to engage one another to enclose the interior cavity of the housing. A fluid channel defined within an outer perimeter of at least one of the first housing portion or the second housing portion. The first and second housing portions are configured to engage with one another to enclose the fluid channel such that the fluid channel is separate from the interior cavity of the housing. Also, a port is disposed on the housing. The port is in communication with the fluid channel and configured to at least supply fluid to the fluid channel or remove fluid from the fluid channel. A shaft is coupled to the housing and extends distally therefrom. An end effector assembly is disposed at a distal end of the shaft.

In an aspect of the present disclosure, the first housing portion and the second housing portion each include a distal end defining a C-shaped aperture, wherein the C-shaped apertures cooperate to define an aperture for receipt of the shaft therethrough upon engagement of the first and second housing portions.

In another aspect of the present disclosure, the first housing portion defines a first fluid channel portion, the second housing portion defines a second fluid channel, and wherein the first and second fluid channel portions cooperate to define the fluid channel upon the engagement of the first and second housing portions. The first and second fluid channel portions each form one-half of the fluid channel. In one embodiment, the fluid channel is disposed in fluid communication with the shaft and configured to facilitate at least one of the supply of fluid adjacent to the end effector assembly or the removal of fluid from adjacent the end effector assembly.

In yet another aspect of the present disclosure, the first housing portion includes a first port portion and the second housing portion includes a second port portion, the first and second port portions are configured to cooperate to form the port upon engagement of the first and second housing portions with one another. In one embodiment, the port may include a luer lock feature disposed thereon.

In still yet another aspect of the present disclosure, a surgical device is provided including a first shaft member and a second shaft member. Where at least one of the first shaft member or the second shaft member includes a housing defining an interior cavity, which includes a first housing portion and second housing portion. The first and second housing portions configured to engage one another to enclose the interior cavity of the housing. A channel is defined within an outer perimeter of at least one of the first housing portion or the second housing portion, wherein the engagement of the first and second housing portions encloses the channel such that the channel is separate from the interior cavity of the housing. Also, an end effector assembly is disposed at a distal end of the first and second shaft members. In one embodiment, the channel is configured as a fluid channel which facilitates at least supplying fluid adjacent to the end effector assembly or removing fluid from adjacent the end effector assembly. In another embodiment, the channel is configured to house at least one electrical wire. The at least one electrical wire is adapted to connect to a source of energy and electrically coupled to the end effector assembly for supplying energy to the end effector assembly.

BRIEF DESCRIPTION OF THE DRAWINGS

Various aspects and features of the present disclosure are described herein with reference to the drawings wherein.

DETAILED DESCRIPTION

Figure 1:
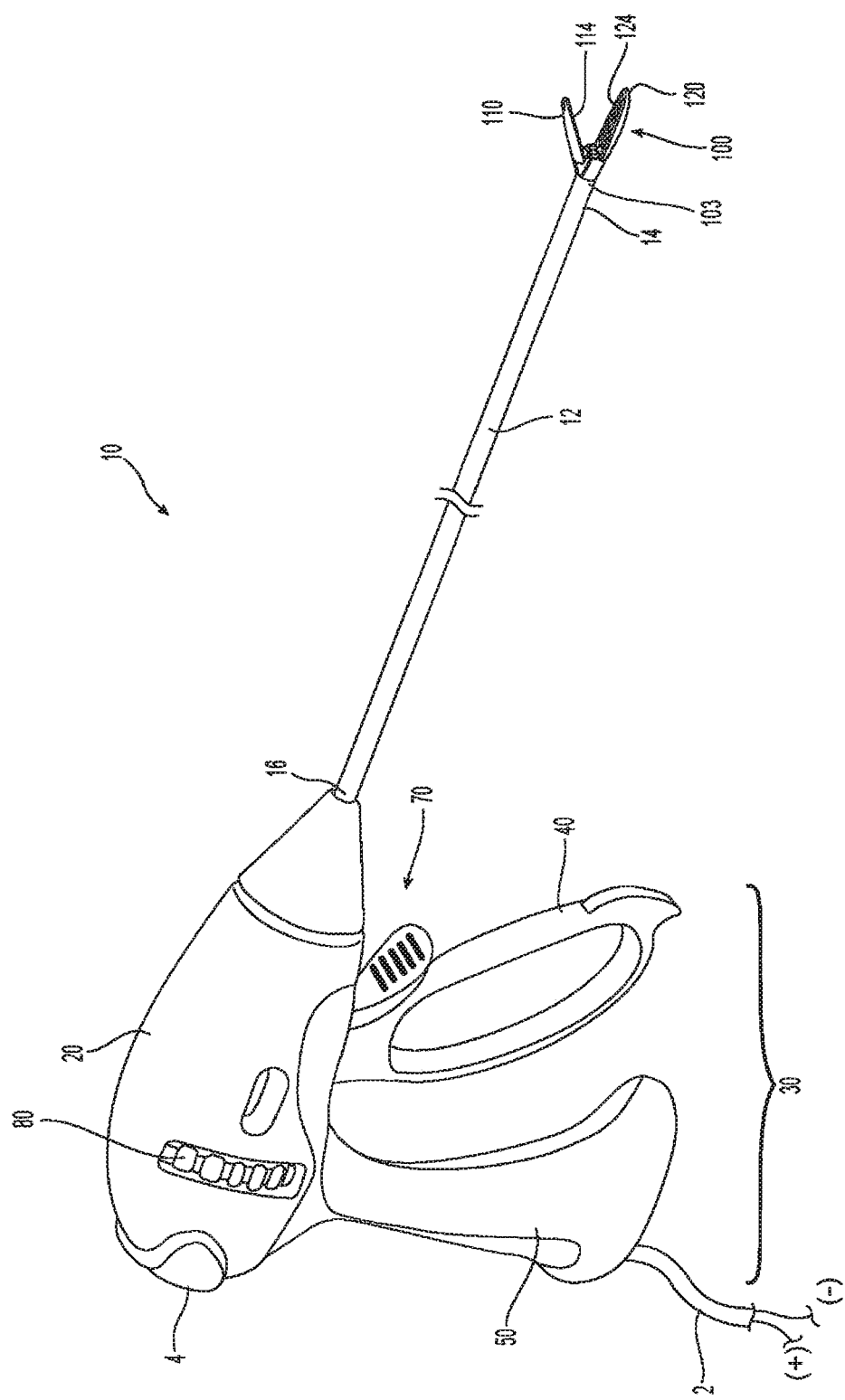
FIG. 1 is a front, side, perspective view of an endoscopic surgical forceps provided in accordance with the present disclosure.

Embodiments of the present disclosure are now described in detail with reference to the drawings in which like reference numerals designate or corresponding elements in each of the several views. As used herein, the term "clinician" refers to a doctor, a nurse, or any other care providers and may include support personnel. Throughout this description, the term "proximal" will refer to the portion of the device or component thereof that is closer to the clinician and the term "distal" will refer to the portion of the device or component thereof that is farthest from the clinician.

Figure 4:
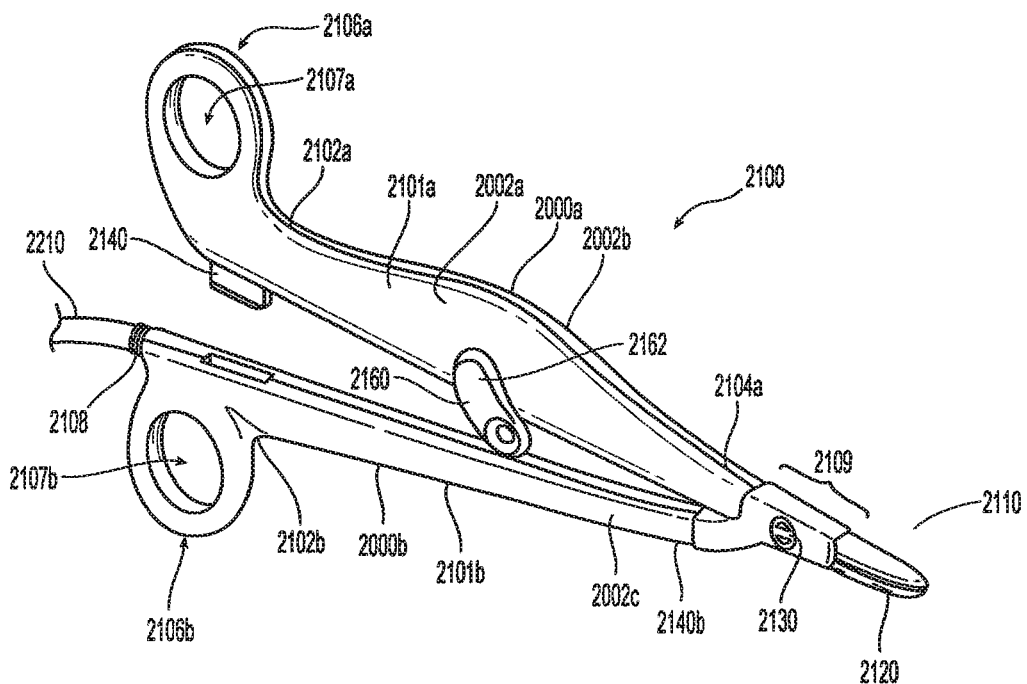
FIG. 4 is a front, side, perspective view of an open surgical forceps provided in accordance with the present disclosure.

Turning to FIGS. 1 and 4, FIG. 1 depicts a handheld, shaft-based, or endoscopic surgical forceps 10 and FIG. 4 depicts a hemostat-style or open surgical forceps 2100. For the purposes herein, either forceps 10, forceps 2100, or any other suitable surgical instrument may be utilized in accordance with the present disclosure. Obviously, different electrical and mechanical connections and considerations apply to each particular type of instrument; however, the aspects and features of the present disclosure remain generally consistent regardless of the particular instrument used.

Referring to FIG. 1, surgical forceps 10 generally includes a housing 20, a handle assembly 30, an actuation assembly 70, a rotating assembly 80, an activation switch 4, and an end effector assembly 100. Forceps 10 further includes a shaft 12 having a distal end 14 configured to mechanically engage end effector assembly 100 and a proximal end 16 that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes an electrical wire (or electrical wires) 28 (FIG. 2) extending therethrough that has sufficient length to extend through housing 20 and operably couple to shaft 12 or other suitable electrical connectors (not shown) in order to provide energy to one or both tissue-treating plates 114, 124 of jaw members 110, 120, respectively. Activation switch 4 is coupled to tissue-treating plates 114, 124 of jaw members 110, 120, respectively, and the source of energy for selectively activating the supply of energy to jaw members 110, 120 for treating, e.g., cauterizing, coagulating/desiccating, and/or sealing, tissue.

Figure 2:
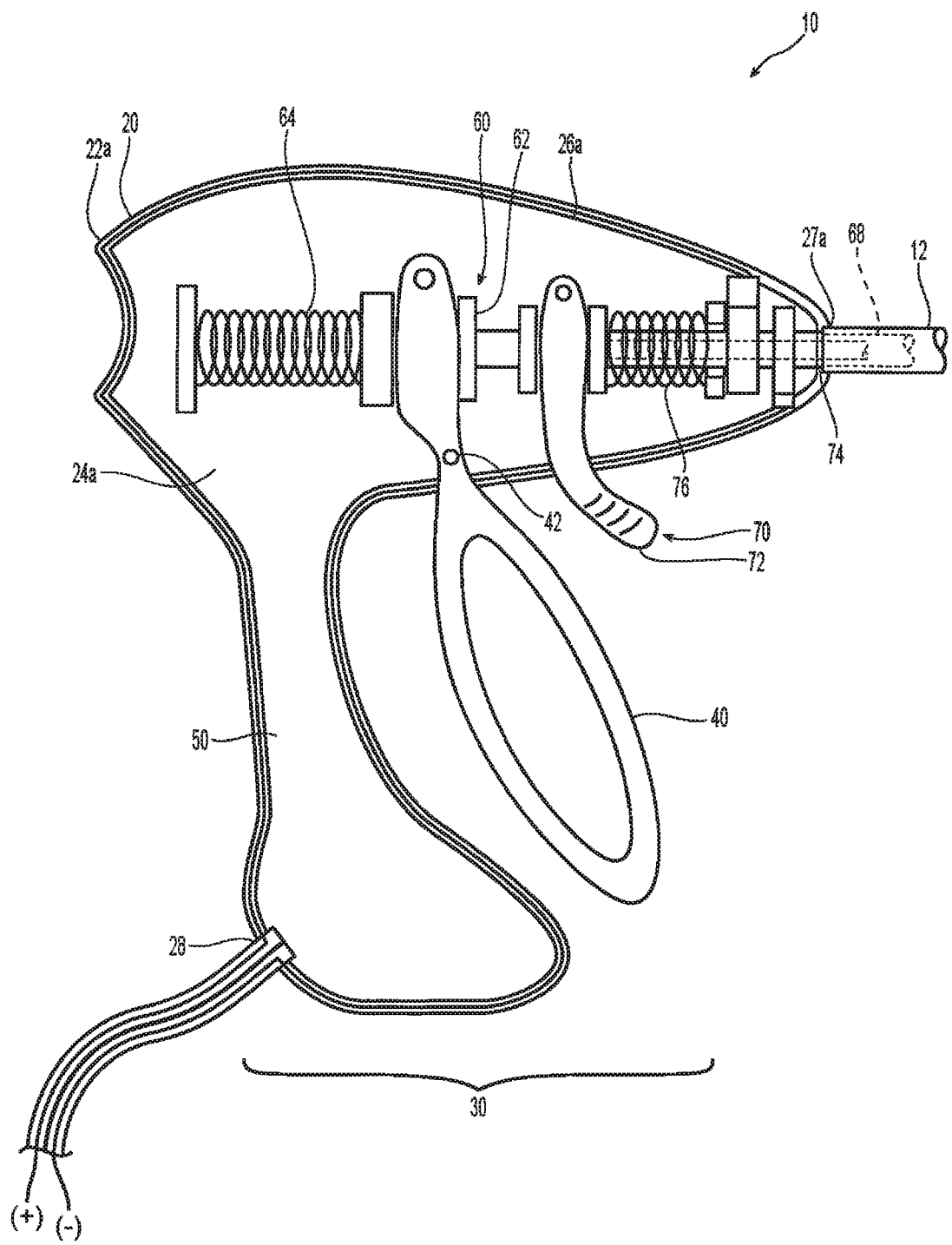
FIG. 2 is a side, cut-away view of the proximal portion of the forceps of FIG. 1, wherein a housing portion and some of the internal components thereof have been removed.

Referring to FIGS. 1 and 2, handle assembly 30 includes fixed handle 50 and a movable handle 40. Fixed handle 50 is integrally associated with housing 20 and handle 40 is movable relative to fixed handle 50. Movable handle 40 of handle assembly 30 is operably coupled to a drive assembly 60 that, together, mechanically cooperate to impart movement of one or both of jaw members 110, 120 about a pivot 103 (FIGS. 6 and 7) between a spaced-apart position and an approximated position to grasp tissue between jaw members 110, 120. In particular, movable handle 40 is coupled to drive bar 68 via a drive mandrel 62 such that movement of movable handle 40 relative to housing 20 effects longitudinal translation of drive bar 68 through housing 20 and shaft 12. The distal end of drive bar 68 is coupled to one or both jaw members 110, 120 such that longitudinal translation of drive bar 68 relative to end effector assembly 100 pivots one or both of jaw members 110, 120 relative to the other. As shown in FIG. 1, movable handle 40 is initially spaced-apart from fixed handle 50 and, correspondingly, jaw members 110, 120 are disposed in the spaced-apart position (see also FIG. 6). Movable handle 40 is depressible from this initial position to a depressed position corresponding to the approximated position of jaw members 110, 120 (see FIG. 7). Further, a biasing member 64 may be disposed within housing 20 and positioned to bias drive bar 68 distally, thereby biasing jaw members 110, 120 towards the spaced-apart position. However, other configurations are also contemplated.

With continued reference to FIGS. 1 and 2, actuation assembly 70 includes a trigger 72 coupled to housing 20 and movable relative thereto between an un-actuated position and an actuated position. More specifically, trigger 72 is operably coupled to an actuation bar 74 such that movement of trigger 72 relative to housing 20 effects longitudinal translation of actuation bar 74 through housing 20 and shaft 12. The distal end of actuation bar 74 is coupled to a knife (not shown) such that longitudinal translation of actuation bar 74 effects translation of the knife relative to end effector assembly 100 between a retracted position, wherein the knife is disposed proximally of end effector assembly 100, and an extended position, wherein the knife extends between jaw members 110, 120 to cut tissue grasped therebetween. Trigger 72, as shown in FIG. 1, is initially disposed in an un-actuated position and, correspondingly, the knife is disposed in the retracted position. Trigger 72 is selectively actuatable from this un-actuated position to an actuated position corresponding to the extended position of the knife for cutting tissue grasped between jaw members 110, 120 of end effector assembly 100. Further, a biasing member 76 may be disposed within housing 20 and positioned to bias actuation bar 74 proximally, thereby biasing the knife towards the retracted position and trigger 72 towards the un-actuated position.

Turning to FIG. 2, housing 20 includes a first housing portion 22*a* and a second housing portion (not shown) of a similar except mirror-image configuration. Accordingly, reference herein will be made to first housing portion 22*a*, keeping in mind that the second housing portion includes similar features. In some embodiments, first housing portion 22*a* and the second housing portion are connected via snap-fitting, ultrasonic welding, or by screws. In other embodiments, first housing portion 22*a* and the second housing portion are adhered together. The adhesive used to adhere first housing portion 22*a* and the second housing portion can be selected from a group consisting of epoxy, acrylic, urethane, and cyanoacrylate; however, it is contemplated that other adhesives or other mechanisms for connecting first housing portion 22*a* and the second housing portion with one another may be utilized.

When first housing portion 22*a* and the second housing portion are aligned and connected, the housing 20 defines an interior cavity, a channel separate from the interior cavity, and an aperture for receipt of the shaft 12. The interior cavity is formed from an interior cavity portion 24*a* defined within first housing portion 22*a* and a corresponding interior cavity portion defined within the second housing portion. Interior cavity is configured to house at least a portion of the internal components of forceps 10 (FIG. 1), e.g., drive assembly 60, actuation assembly 70, etc. The channel is defined by a channel portion 26*a* formed within first housing portion 22*a* and a corresponding channel portion formed within the second housing portion. Channel portion 26*a* can be located adjacent an outer perimeter of first housing portion 22*a* and may be defined adjacent the entire outer perimeter of first housing portion 22*a* or adjacent a portion of the outer perimeter of first housing portion 22*a*. The channel may be configured to house one or more electrical conductors, e.g., one or more of the electrical wires 28 from cable 2 (FIG. 1), such that the electrical wire 28 extends through the channel to allow electrical wire 28 to be in electrical communication with shaft 12 or other electrical connectors (not shown), e.g., wires or other conductive structures, in order to provide energy to one or both tissue-treating plates 114, 124 of jaw members 110, 120, respectively (see FIGS. 1 and 6). Further, the channel is formed so that it is separated from the interior cavity, thus, when electrical wire 28 is housed within the channel it is also separated from the interior cavity. In some embodiments, the channel is sealed off from the interior cavity as well as the exterior of housing 20. The aperture is formed from a C-shaped aperture 27*a* defined within first housing portion 22*a* and a corresponding C-shaped aperture defined within the second housing portion. The aperture is configured for the insertion of shaft 12. By inserting shaft 12 within the aperture, shaft 12 may interact with the other internal components of forceps 10, e.g., drive assembly 60, actuation assembly 70, etc., and allows wire 28 to be in electrical communication with shaft 12, as stated above. Housing wire 28 within the channel is advantageous in that it allows separation between the electrical conductor(s) and the other components within the housing, thus inhibiting accidental damage to and/or wearing of the electrical conductors during use, cleaning sterilization, reprocessing, etc. Such a configuration also facilitates assembly in that the need for wire routing in and around the various components within the interior cavity is eliminated.

Figure 3:
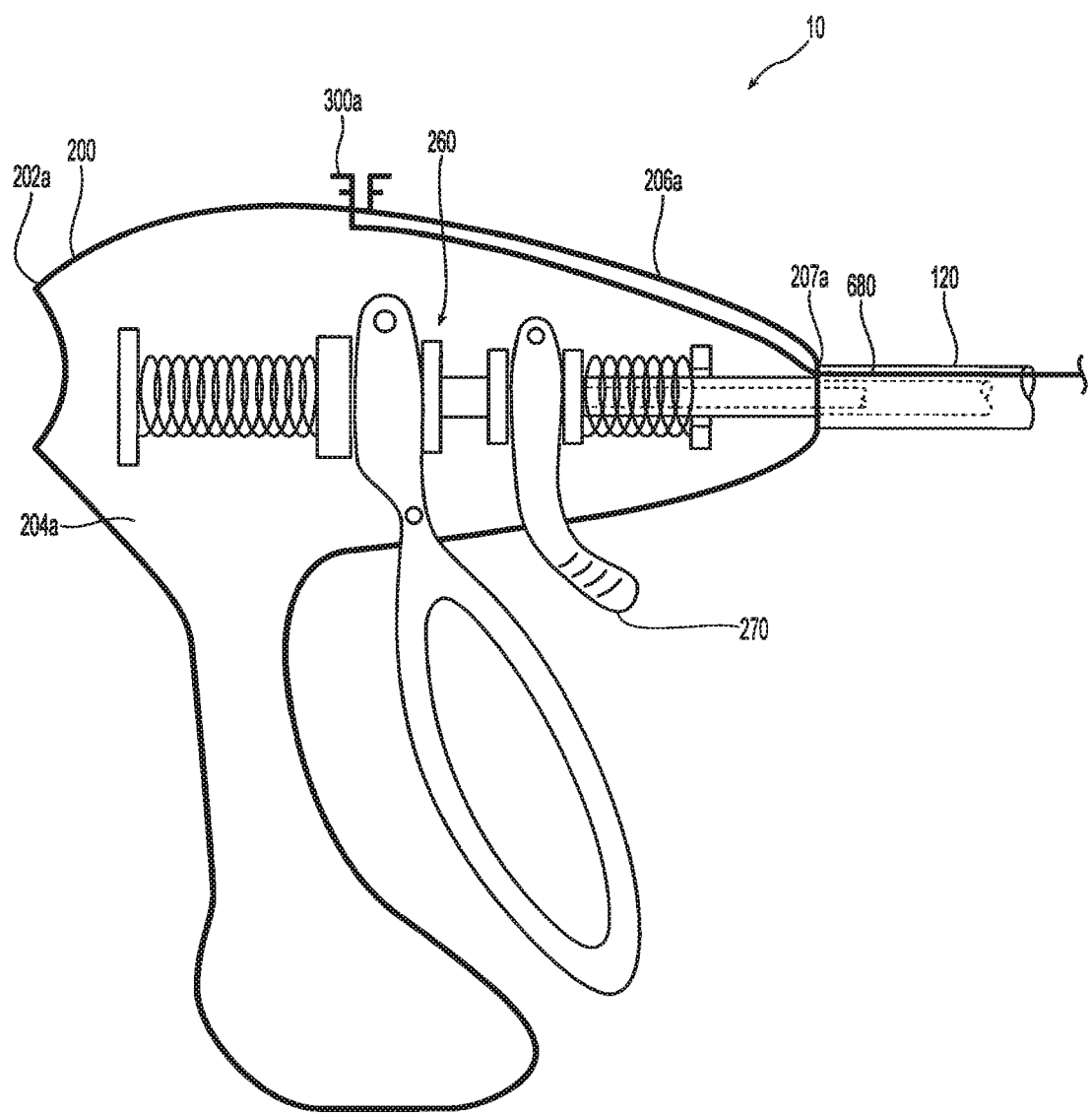
FIG. 3 is a side, cut-away view of the proximal portion of the forceps of FIG. 1, including another housing, wherein a housing portion thereof and some of the internal components of the forceps have been removed.

Referring to FIG. 3, another housing 200 configured for use with surgical forceps 10 (FIG. 1) is provided in accordance with the present disclosure. Housing 200 is similar to housing 20 and, thus, similar features are not detailed hereinbelow to avoid unnecessary repetition. Housing 200 includes a first housing portion 202*a* and a second housing portion (not shown) of a similar except mirror-image configuration. Accordingly, reference herein will be made to first housing portion 202*a*, keeping in mind that the second housing portion includes similar features.

When housing 200 is aligned and connected, housing 200 forms an interior cavity, a fluid channel separate from the interior cavity, and an aperture for receipt of the shaft 120. Housing 200 is connected, e.g., according to any of the embodiments detailed above or in any other suitable configuration, so as to establish a fluid-tight seal about the fluid channel to inhibit the escape of fluid therefrom. The interior cavity is formed by a cavity portion 204*a* of first housing portion 202*a* and a corresponding cavity portion of the second housing portion. The fluid channel is formed by a channel portion 206*a* of first housing portion 202*a* and a channel portion of the second housing portion. Channel portion 206*a* is defined adjacent to an outer perimeter of first housing portion 202*a* and may be defined adjacent the entire outer perimeter of first housing portion 202*a* or may be defined adjacent a portion of the outer perimeter of first housing portion 202*a*. In embodiments where channel portion 206*a* is defined adjacent a portion of the outer perimeter of first housing portion 202*a* channel portion 206*a* may be disposed in a superior or inferior location adjacent the outer perimeter of first housing portion 202*a*, and/or may extend vertically along the outer perimeter of first housing portion 202*a*. The fluid channel is disposed in fluid communication with shaft 120 and/or another conduit 680 extending through or about shaft 120. The aperture is formed from a C-shaped aperture 207*a* defined within first housing portion 202*a* and a corresponding C-shaped aperture defined within the second housing portion. The aperture is configured for the insertion of shaft 120. By inserting shaft 120 within aperture 207, shaft 120 may interact with the other internal components of forceps 10, e.g., drive assembly 260, actuation assembly 270, etc., and allows the fluid channel to be disposed in fluid communication with shaft 120, as stated above.

The fluid channel is configured to supply fluid, e.g., liquid, gas, or a mixture of gas and liquid, through shaft 120 (or other conduit) to the end effector assembly, e.g., end effector assembly 100, remove fluid from the end effector assembly, e.g., end effector assembly 100 through shaft 120 (or other conduit), or both. Fluid is supplied to end effector assembly 100 for multiple purposes, such as flushing out shaft 120 for reprocessing or cleaning, sterilizing the interior of shaft 120 and/or end effector assembly 100, cooling the end effector assembly 100, irrigating tissue disposed between or adjacent jaw members 110, 120 of end effector assembly 100, supplying fluid to facilitate treating tissue disposed between jaw members 110, 120 of end effector assembly 100 (e.g., disinfecting tissue, introducing a marking agent, and/or introducing a coagulant), actuation of a function (e.g., throwing a knife or supplying pressure to tissue), and drying shaft 120 and/or end effector assembly 100. Extracting fluid from end effector assembly 100 is performed for multiple purposes, such as incorporating suction into end effector assembly 100, cooling end effector assembly 100, and removing smoke from shaft 120 and/or the surgical site.

A port is further included on housing 200. The port may be located on a superior portion of housing 200 and in communication with the fluid channel. The port is formed from a first port portion 300a integrally formed with first housing portion 202a and a second port portion integrally formed with the second housing portion. First port portion 300a and the second port portion may be connected similarly as first housing portion 202a and the second housing portion. The port may include a luer lock feature which enables a leak-free connection of a fluid supply or return line to the fluid channel. Providing the fluid channel and the port integral with housing 200 is advantageous in that it obviates the need of a separate tube extending through the interior cavity of housing 200 and inhibits accidental damage to and/or wearing of the fluid channel. Such a configuration also facilitates assembly in that the fluid channel and port are formed upon connecting first housing portion 202a and the second housing portion with one another.

Figure 6:
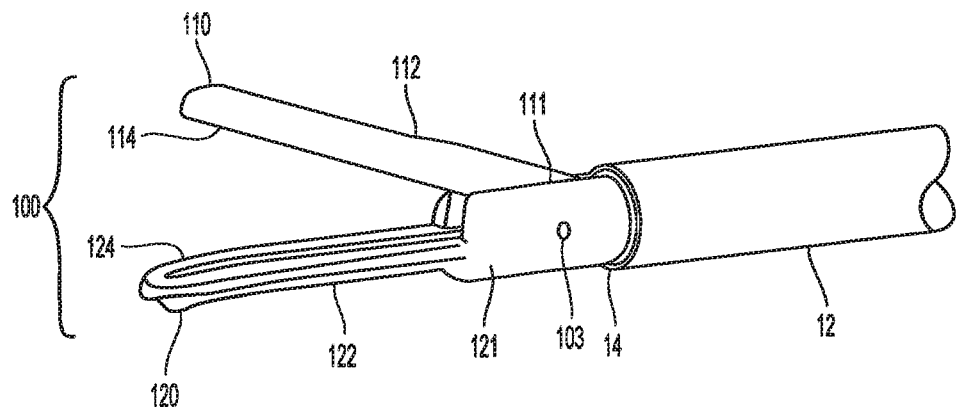
FIG. 6 is a front, side, perspective view of the end effector assembly of the forceps of FIG. 1, disposed in a spaced-apart position.
Figure 7:
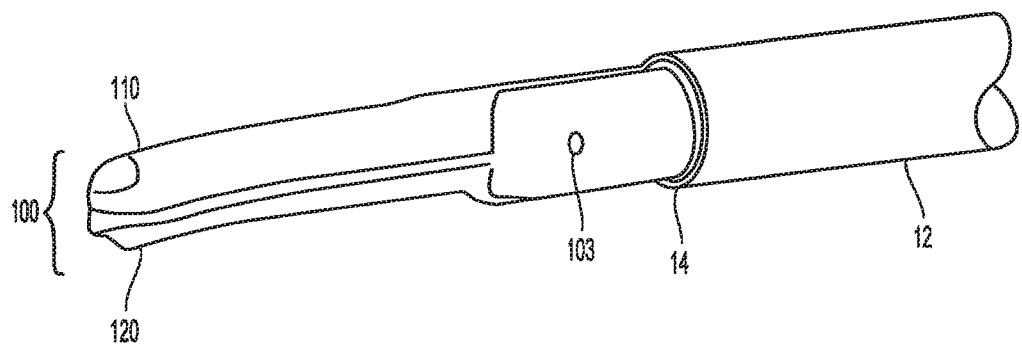
FIG. 7 is a front, side, perspective view of the surgical forceps of FIG. 1, disposed in an approximated position.

Referring to FIG. 4, an open surgical forceps 2100 provided in accordance with the present disclosure is shown including two elongated shaft members 2101a, 2101b, each having a proximal end 2102a, 2102b, and a distal end 2104a, 2104b, respectively. Forceps 2100 is configured for use with an end effector assembly 2109 similar to end effector assembly 100 (FIGS. 1, 6, and 7). More specifically, end effector assembly 2109 includes first and second jaw members 2110, 2120 attached to respective distal ends 2104a, 2104b of shaft members 2101a, 2101b. Jaw members 2110, 2120 are pivotably connected about a pivot 2130. Each shaft member 2101a, 2101b includes a handle 2106a, 2106b disposed at the proximal end 2102a, 2102b thereof. Each handle 2106a, 2106b defines a finger hole 2107a, 2107b therethrough for receiving a finger of the clinician. As can be appreciated, finger holes 2107a, 2107b facilitate movement of the shaft members 2101a, 2101b relative to one another to, in turn, pivot jaw members 2110, 2120 from the spaced-apart position, wherein jaw members 2110, 2120 are disposed in spaced relation relative to one another, to the approximated position, wherein jaw members 2110, 2120 cooperate to grasp tissue therebetween.

One of the shaft members 2101a, 2101b of forceps 2100, e.g., shaft member 2101b, includes a proximal shaft connector 2108 configured to connect the forceps 2100 to a source of energy (not shown), e.g., a generator. Proximal shaft connector 2108 secures a cable 2210 to forceps 2100 such that the clinician may selectively supply energy to jaw members 2110, 2120 for treating tissue and for energy-based tissue cutting. More specifically, an activation switch 2140 is provided for supplying energy to jaw members 2110, 2120 to treat tissue upon sufficient approximation of shaft members 2102a, 2102b, e.g., upon activation of activation switch 2140 via shaft member 2102b.

Forceps 2100 further includes an actuation assembly 2160 including a trigger 2162 coupled to one of the shaft members, e.g., shaft member 2101b, and movable relative thereto between an un-actuated position and an actuated position for transitioning end effector assembly 2109 between an un-actuated condition and an actuated condition, similarly as with end effector assembly 100 (FIGS. 6 and 7).

Figure 5:
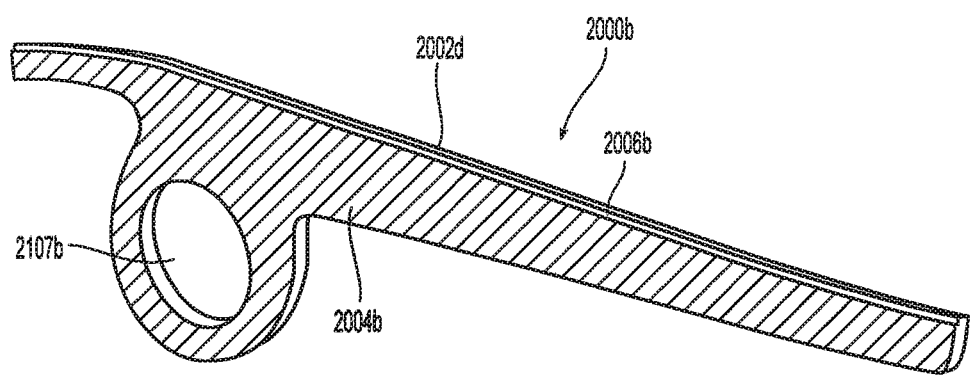
FIG. 5 is a side, cut-away view of a shaft member of the forceps of FIG. 4.

With additional reference to FIG. 5, elongated shaft member 2101a defines a housing 2000a and/or elongated shaft member 2101b defines a housing 2000b. Housing 2000a is formed by a first housing portion 2002a and second housing portion 2002b in any suitable fashion such as those detailed above. Housing 2000b is formed by a first housing portion 2002c and a second housing portion 2002d in any suitable fashion such as those detailed above. One or both of housings 2000a, 2000b defines an interior cavity 2004b (the interior cavity of housing 2000a is not shown), respectively. Additionally, one or both of housings 2000a, 2000b defines a channel 2006b (the channel of housing 2000a is not shown) that may be configured similarly as detailed above. The channel of housing 2000a and channel 2006b of housing 2000b may be provided for similar or different purposes. For example, the channel of housing 2000a may serve as a fluid channel to allow a supply of fluid to end effector assembly 2109, removal of fluid from end effector assembly 2109, or both, similarly as detailed above, and may also include a port (not shown) formed with housing 2000a. Channel 2006b of housing 2000b, on the other hand, may be configured to house an electrical wire (not shown) from cable 2210 and proximal shaft connector 2108 of shaft member 2101b so as to provide energy to one or both of jaw members 2110, 2120 of end effector assembly 2109, similarly as detailed above.

With reference to FIGS. 6 and 7, end effector assembly 100 of forceps 10 (FIG. 1) is shown, although end effector assembly 2109 (FIG. 4) of forceps 2100 (FIG. 4) is similar and functions in a similar manner. For purposes of simplicity, only end effector assembly 100 is described hereinbelow, as configured for use with forceps 10 (FIG. 1).

Each jaw member 110, 120 of end effector assembly 100 includes a jaw frame having a proximal flange portion 111, 121, an outer insulative jaw housing 112, 122 disposed about the distal portion (not explicitly shown) of each jaw frame, and a tissue-treating plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw frames are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-treating plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 (FIG. 1) and the source of energy (not shown), e.g., via the wires 28 extending from cable 2 (FIG. 1) through forceps 10 (FIG. 1) via the channel (FIG. 2), such that energy may be selectively supplied to tissue-treating plate 114 and/or tissue-treating plate 124 and conducted therebetween and through tissue disposed between jaw members 110, 120 to treat tissue.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
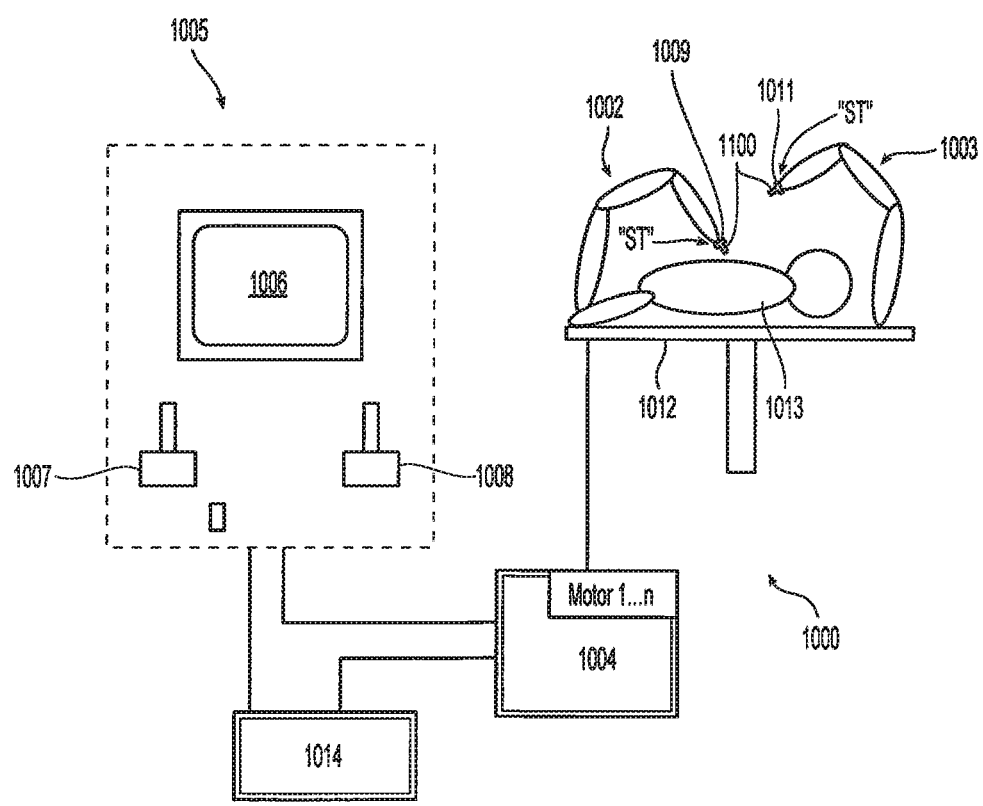
FIG. 8 is a schematic of a robotic surgical system configured to work with surgical forceps of this present disclosure.

Referring to FIG. 8, a medical work station is shown generally as work station 1000 and may generally include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of the embodiments disclosed hereinabove.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a housing defining an interior cavity and including a first housing portion and a second housing portion, the first and second housing portions configured to engage one another to enclose the interior cavity of the housing;
    a drive assembly disposed within the interior cavity of the housing;
    a channel defined within an outer perimeter of at least one of the first housing portion or the second housing portion, wherein engagement of the first and second housing portions encloses the channel such that the channel is fluidly separate from the interior cavity of the housing;
    at least one electrical wire housed within the channel, wherein the at least one electrical wire is adapted to connect to a source of energy;
    a shaft coupled to the housing and extending distally therefrom; and
    an end effector assembly disposed at a distal end of the shaft, wherein the end effector assembly is electrically coupled to the at least one electrical wire for supplying energy to the end effector assembly.

2. The surgical instrument according to claim 1, wherein the first housing portion and the second housing portion each include a distal end defining a C-shaped aperture, wherein the C-shaped apertures cooperate to define an aperture for receipt of the shaft therethrough upon engagement of the first and second housing portions.

3. The surgical instrument according to claim 1, wherein the first housing portion defines a first channel portion, wherein the second housing portion defines a second channel portion, and wherein the first and second channel portions cooperate to define the channel upon engagement of the first and second housing portions.

4. The surgical instrument according to claim 3, wherein the first and second channel portions each form one-half of the channel.

5. The surgical instrument according to claim 1, wherein the first and second housing portions are configured to engage one another via snap-fitting.

6. The surgical instrument according to claim 1, wherein the first and second housing portions are configured to engage one another via an adhesive.

7. The surgical instrument according to claim 6, wherein the adhesive is selected from a group consisting of epoxy, acrylic, urethane, and cyanoacrylate.

8. The surgical instrument according to claim 1, further comprising a handle assembly including a fixed handle and a movable handle, the fixed handle integrally associated with the housing, and the channel is further defined around an outer perimeter of the fixed handle.

9. A surgical instrument, comprising:
a housing defining an interior cavity and including a first housing portion and a second housing portion, the first and second housing portions configured to engage one another to enclose the interior cavity of the housing;
a fluid channel defined within an outer perimeter of at least one of the first housing portion or the second housing portion, wherein engagement of the first and second housing portions encloses the fluid channel such that the fluid channel is fluidly separate from the interior cavity of the housing, both the fluid channel and the internal cavity extending to a distal end of the housing;
a port disposed on the housing, the port in communication with the fluid channel and configured to at least one of supply fluid to the fluid channel or remove fluid from the fluid channel;
a shaft coupled to the distal end of the housing and extending distally therefrom; and
an end effector assembly disposed at a distal end of the shaft.

10. The surgical instrument according to claim 9, wherein the first housing portion and the second housing portion each include a distal end defining a C-shaped aperture, wherein the C-shaped apertures cooperate to define an aperture for receipt of the shaft therethrough upon engagement of the first and second housing portions.

11. The surgical instrument according to claim 9, wherein the first housing portion defines a first fluid channel portion, wherein the second housing portion defines a second fluid channel portion, and wherein the first and second fluid channel portions cooperate to define the fluid channel upon engagement of the first and second housing portions.

12. The surgical instrument according to claim 11, wherein the first and second fluid channel portions each form one-half of the fluid channel.

13. The surgical instrument according to claim 9, wherein the first housing portion includes a first port portion and the second housing portion includes a second port portion, the first and second port portions cooperating to form the port upon engagement of the first and second housing portions with one another.

14. The surgical instrument according to claim 13, wherein the port includes a luer lock feature disposed thereon.

15. The surgical instrument according to claim 9, wherein the fluid channel is disposed in fluid communication with the shaft and configured to at least one of supply the fluid through the shaft adjacent to the end effector assembly or remove the fluid from adjacent the end effector assembly through the shaft.

16. The surgical instrument according to claim 9, further comprising a drive assembly disposed within the interior cavity of the housing, and the end effector assembly includes two jaw members, one or both of the jaw members pivotable with respect to the other via actuation of the drive assembly.

17. A surgical instrument, comprising,
first and second shaft members, each of the first and second shaft members including a housing defining an interior cavity and including a first housing portion and a second housing portion, the first and second housing portions configured to engage one another to enclose the interior cavity of the housing;
a channel defined within an outer perimeter of at least one of the first housing portion or the second housing portion of each of the first and second shaft members, wherein engagement of the first and second housing portions encloses the channel such that the channel is fluidly separate from the interior cavity of the housing; and
an end effector assembly disposed at a distal end of the first and second shaft members.

18. The surgical instrument according to claim 17, wherein the channel of the first or second shaft member is a fluid channel configured to at least one of supply fluid adjacent to the end effector assembly or remove fluid from adjacent the end effector assembly.

19. The surgical instrument according to claim 17, further comprising at least one electrical wire housed within the channel of the first or second shaft member, wherein the at least one electrical wire is adapted to connect to a source of energy and electrically coupled to the end effector assembly for supplying energy to the end effector assembly.

20. The surgical instrument according to claim 17, wherein the channel of the first or second shaft member extends longitudinally along the outer perimeter adjacent a surface of the first or second shaft member facing the other of the first or second shaft members.

* * * * *